(12) United States Patent
Cao et al.

(10) Patent No.: US 6,582,507 B1
(45) Date of Patent: Jun. 24, 2003

(54) BIOCL PIGMENT

(75) Inventors: Paul B. Cao, Ossining, NY (US); Michael Venturini, Yorktown Hts., NY (US)

(73) Assignee: Engelhard Corporation, NJ (US)

( * ) Notice: Subject to any disclaimer, the term of this patent is extended or adjusted under 35 U.S.C. 154(b) by 0 days.

(21) Appl. No.: 10/222,844

(22) Filed: Aug. 19, 2002

(51) Int. Cl.$^7$ .............................................. C04B 14/00

(52) U.S. Cl. ...................... 106/479; 106/415; 106/419; 106/456; 106/31.9; 106/31.65

(58) Field of Search ................................ 106/415, 419, 106/456, 479, 439, 31.9, 31.65

(56) References Cited

U.S. PATENT DOCUMENTS

| | | | |
|---|---|---|---|
| 3,822,141 A | | 7/1974 | Kaufman |
| 3,980,491 A | | 9/1976 | Eberts |
| 5,149,369 A | * | 9/1992 | Eberts et al. ................ 106/479 |
| 5,344,488 A | * | 9/1994 | Reynders et al. ........... 106/425 |

* cited by examiner

*Primary Examiner*—C. Melissa Koslow
*Assistant Examiner*—Shalie Manlove
(74) *Attorney, Agent, or Firm*—Dickstein, Shapiro, Morin & Oshinsky, LLP.

(57) ABSTRACT

A bismuth oxychloride effect pigment has a zinc oxide or microfine titanium dioxide particulate at about the surface of the crystals of the bismuth oxychloride. The pigment is prepared by, for instance, growing the bismuth oxychloride crystals, and adding the particulate before the hydrolysis is complete.

25 Claims, No Drawings

BIOCL PIGMENT

BACKGROUND OF THE INVENTION

Laminar or plate-like pigments which impart a pearly or nacreous luster into objects on which or in which they are used are known as "effect" pigments, and have also been known as pearlescent pigments or nacreous pigments. These effect pigments include naturally occurring substances such as pearlescence, a mixture of guanine and hypoxanthine which is obtained from the scales of fish, as well as various synthetic materials. The effect pigments which are most often encountered commercially are titanium dioxide-coated mica and iron oxide-coated mica. Other synthetic effect pigments which have been developed for both cosmetic and industrial use include materials such as bismuth oxychloride and lead carbonate.

Bismuth oxychloride has been used as an effect pigment in a number of fields. It is used, for instance, as a pigment in cosmetics, such as nail enamels and lipsticks, and it is also used to pigment plastics and paints. The coating of a bismuth oxychloride-coated mica pigment with hydrous titanium hydroxide is described in U.S. Pat. No. 3,980,491 and the coating of bismuth oxychloride with zinc oxide is described in U.S. Pat. No. 5,344,488. Coprecipitation of bismuth oxychloride and titanium dioxide on a mica substrate is described in U.S. Pat. No. 3,822,141. In order to extend the range of applications, bismuth oxychloride pigments have been coated with such materials as 2-hydroxy benzophenones and rare earth metals in order to impart ultraviolet stability or weather fastness properties to the effect pigment. The result of coating a BiOCl pigment itself, however, is that some of the natural luster and brightness to be lost. It is therefore desired to improve the light stability of the bismuth oxychloride while achieving a better brightness.

It is accordingly the object of the present invention to provide an improved bismuth oxychloride effect pigment with better light stability and brightness and to provide a method for producing such a pigment.

SUMMARY OF THE INVENTION

The present invention relates to an improved bismuth oxychloride effect pigment and a process for its production. More particularly, the invention relates to an improved bismuth oxychloride effect pigment having an embedded particulate of microfine titanium dioxide or zinc oxide at about the surface thereof, which can be produced by hydrolyzing a soluble bismuth salt in the presence of chloride and adding the particulate to the hydrolyzation reaction mixture before the formation of the bismuth oxychloride is complete.

DESCRIPTION OF THE INVENTION

In accordance with the present invention, the conventional production of bismuth oxychloride crystals is modified by adding a particulate to the reaction mixture before the formation of the crystals is complete or alternatively, by ending the BiOCl crystal formation, adding a dispersion of the particulate and thereafter adding an aluminum or rare earth metal salt to lock in (cement) the particulate to the crystal.

Bismuth oxychloride crystals are typically produced by combining a soluble bismuth compound with a source of chloride under acid conditions. Hydrolyzation occurs at a rate which is dependent on the concentrations of the reactants, pH and temperature. The material which is most often employed is bismuth nitrate although any soluble bismuth compound can be used. To prevent premature hydrolysis and precipitation of insoluble bismuth compounds, the bismuth salt is usually employed in the form of an aqueous acidic solution. For this purpose, the solution typically contains a compatible mineral or other strong acid. Hydrochloric acid and a mixture of hydrochloric and nitric acids are particularly convenient since they serve as a source of the chloride ions which are used to form the bismuth oxychloride. The bismuth compound is hydrolyzed by maintaining the acidity within desired limits, usually about pH 1, by adding a suitable base to neutralize acid which forms during the hydrolysis reaction. The base most often used is an alkali metal hydroxide, particularly sodium hydroxide, but other soluble sources of hydroxyl ions, such as a strongly basic amine or a base precursor such as urea, can also be used.

The preparation of the bismuth oxychloride crystals is generally effected at a temperature between about 50° C. and 100° C. and more preferably about 60–80° C. Usually the soluble bismuth salt solution and the base are pumped into an aqueous acidic reservoir. Any desired bismuth oxychloride crystal size can be realized by regulating the amount of the bismuth solution which is used.

In a preferred procedure, a preformed particulate is added to the hydrolyzation reaction mixture before the formation of the desired bismuth oxychloride crystals is complete. So that the particulate is at or near the surface of the effect pigment, the bismuth oxychloride formation process is allowed to achieve about 80 to 95% completion, preferably about 85 to 90% completion, before the addition is effected. The particulate can be either microfine zinc oxide or titanium dioxide, i.e., having a particle size of less than about 500 nm. The particle size of the microfine particulate is usually at least about 5 nm, preferably at least about 10 nm and most preferably at least about 100 nm. While the particulate can be added as such, it is generally more convenient to disperse the particulate in a compatible liquid such as water or, more preferable, the liquid in which the bismuth salt was dissolved. The concentration of the particulate in the resulting slurry can be varied as desired and the viscosity is generally the controlling factor, with that which allows easy processing of the slurry being selected. Typically, the concentration of the particulate in the slurry is about 1 to 10%.

Alternatively, it is possible to finish the BiOCl crystal formation before adding the particulate but in this instance additional steps and reagents are necessary. The pH is raised to, for instance, at least about 2 to ease materials handling and then a dispersion of the particulate is added. Next, a rare earth metal salt or an aluminum salt, or a combination of salts, is introduced into the slurry and the pH is further raised to an effective deposition value, for example, to at least about 7 in the case of an aluminum salt and to at least about 10 in the case of a rare earth metal salt. The nitrate is the preferred salt. While any rare earth metal can be used, it is preferred to employ cerium.

The amount of the particulate added to the bismuth oxychloride slurry in either process is such that the particulate will generally range from about 1 to 20 weight percent, preferably about 5 to 15 weight percent, based on the weight of the bismuth salt being employed. This results in the incorporation of about 1 to 20 weight, preferably about 5 to 15 weight percent, particulate based on the total weight of the final pigment. Since the particulate is added before the formation of the BiOCl is complete or the "lock-in" procedure is used, the particulate is embedded or bound to the effect pigment at or near the BiOCl surface but does not form a smooth and continuous coating on that surface. As a result, the inherent brightness of the BiOCl effect pigment is substantially retained while at the same time, an improved light stability is achieved.

At the end of the BiOCl preparation, the resulting pigment is recovered from the slurry in which it was formed in any convenient fashion. For example, the pigment can be filtered and then washed with water until substantially free of salt. Alternatively, a settling and decanting procedure can be employed. The pigment can be dried by heating if desired.

The resulting BiOCl effect pigment is thereafter processed in the conventional manner into various types of finished products. For example, the filter cake can be dried to produce a powdered product either with or without the addition of a dispersing agent. Alternatively, the filter cake can be flushed with an oil such as castor oil or mineral oil, which causes the pigment originally wet with water to become a pigment wet with oil.

The resulting bismuth oxychloride can be employed in the same manner as the previously known bismuth oxychloride effect pigments have been employed. For example, it can be used in cosmetics as well as paints and coatings. The plurality of crystals in the products made by the present inventive process have been found to be more homogeneous than conventional bismuth oxychloride effect pigments, combining brightness with enhanced ultraviolet light stability. This increases the ability to use the material in automotive paint and other outdoor applications.

Products of this invention have an unlimited use in all types of automotive and industrial paint applications, especially in the organic color coating and inks field where deep color intensity is required. For example, these pigments can be used in mass tone or as styling agents to spray paint all types of automotive and non-automotive vehicles. Similarly, they can be used on all clay/formica/wood/glass/metal/enamel/ceramic and non-porous or porous surfaces. The pigments can be used in powder coating compositions. They can be incorporated into plastic articles geared for the toy industry or the home. These pigments can be impregnated into fibers to impart new and esthetic coloring to clothes and carpeting. They can be used to improve the look of shoes, rubber and vinyl/marble flooring, vinyl siding, and all other vinyl products. In addition, these colors can be used in all types of modeling hobbies.

The above-mentioned compositions in which the compositions of this invention are useful are well known to those of ordinary skill in the art. Examples include printing inks, nail enamels, lacquers, thermoplastic and thermosetting materials, natural resins and synthetic resins. Some non-limiting examples include polystyrene and its mixed polymers, polyolefins, in particular, polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

For a well-rounded introduction to a variety of pigment applications, see Temple C. Patton, editor, The Pigment Handbook, volume II, Applications and Markets, John Wiley and Sons, New York (1973). In addition, see for example, with regard to ink: R. H. Leach, editor, The Printing Ink Manual, Fourth Edition, Van Nostrand Reinhold (International) Co. Ltd., London (1988), particularly pages 282–591; with regard to paints: C. H. Hare, Protective Coatings, Technology Publishing Co., Pittsburgh (1994), particularly pages 63–288. The foregoing references are hereby incorporated by reference herein for their teachings of ink, paint and plastic compositions, formulations and vehicles in which the compositions of this invention may be used including amounts of colorants. For example, the pigment may be used at a level of 10 to 15% in an offset lithographic ink, with the remainder being a vehicle containing gelled and ungelled hydrocarbon resins, alkyd resins, wax compounds and aliphatic solvent. The pigment may also be used, for example, at a level of 1 to 10% in an automotive paint formulation along with other pigments which may include titanium dioxide, acrylic lattices, coalescing agents, water or solvents. The pigment may also be used, for example, at a level of 20 to 30% in a plastic color concentrate in polyethylene.

In the cosmetic field, these pigments can be used in the eye area and in all external and rinse-off applications. Thus, they can be used in hair sprays, face powder, leg-makeup, insect repellent lotion, mascara cake/cream, nail enamel, nail enamel remover, perfume lotion, and shampoos of all types (gel or liquid). In addition, they can be used in shaving cream (concentrate for aerosol, brushless, lathering), skin glosser stick, skin makeup, hair groom, eye shadow (liquid, pomade, powder, stick, pressed or cream), eye liner, cologne stick, cologne, cologne emollient, bubble bath, body lotion (moisturizing, cleansing, analgesic, astringent), after shave lotion, after bath milk and sunscreen lotion.

For a review of cosmetic applications, see Cosmetics: Science and Technology, 2nd Ed., Eds: M. S. Balsam and Edward Sagarin, Wiley-Interscience (1972) and deNavarre, The Chemistry and Science of Cosmetics, 2nd Ed., Vols 1 and 2 (1962), Van Nostrand Co. Inc., Vols 3 and 4 (1975), Continental Press, both of which are hereby incorporated by reference.

In order to further illustrate the invention, various examples are being set forth below. In these examples as well as throughout the balance of this specification and claims, all temperatures are in degrees Centigrade and all parts and percentages are by weight unless otherwise indicated.

EXAMPLE 1

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

The hydrolysis reaction under these conditions generally take about 80 minutes for the BiOCl formation to be complete. After about 72 minutes had elapsed, 360 ml of an aqueous slurry containing 5% of microfine titanium dioxide was introduced into the aqueous bismuth oxychloride crystal slurry and then the hydrolysis reaction was allowed to continue to completion. This took about an additional 8 minutes. Then, the resulting pigment was recovered by concentrating the crystals present in the aqueous phase of the slurry by settling and removing the supernatant.

In order to evaluate the resulting pigment for light stability, the crystals are flushed into an organic phase which consisted of a ketone ester and aromatic solvents, followed by being dispersed in an organic soluble resin at a crystal content of 60% by weight. Thereafter the dispersed crystals are incorporated into an acrylic-melamine/formaldehyde baking enamel such that the amount of crystals in the enamel is 10% weight of the total resin solids in the enamel. The enamel dispersion is then sprayed on Bonderite 40 treated cold rolled and polished steel panels primed with a low film build cathodic electrodeposition primer. Wet on wet coats were applied so that the dried film thickness is in the range of about 0.002 to 0.003 cm (about 0.9 to 1.1 mils). This is followed by an acrylic melamine/formaldehyde clear coat of about 0.04 to 0.05 cm (about 1.5 to 2 mils) dry film thickness. The panels are then baked for 30 minutes at 250° F. in a forced air oven.

An evaluation test is carried out by placing partly masked panels in a Cleveland chamber and exposing them to alternate cycles of 8 hours of ultraviolet light exposure and 4 hours of water condensation for one week. Changes in appearance of the panels were characterized by measuring the CIE L*a*b* values. This system is described in the text "The Measurement of Appearance", 2nd ed., Hunter and Harold, editors, John Wiley & Sons, 1987. The system involves measuring a lightness-darkness component designated L*, a red-green component designated a* and a yellow-blue component designated b*. The difference in color, designated DE* is calculated using the equation $$DE^* = [(DL^*)^2 + (Da^*)^2 + (Db^*)^2]^{1/2}$$

in which DL*, Da* and Db* represents the difference in L*, A* and b* values between the exposed and unexposed sections of the panel. The higher the value of DE*, the greater the change in appearance between the exposed and unexposed sections of the panel. Conversely, a lower DE* indicates increased light stability. A DE* of less than 1 is generally not apparent to the naked eye.

The DE* of a panel using the pigment of this example was 2.5 compared to a value of 7.1 realized using a BiOCl without particulate.

EXAMPLE 2

The procedure of Example 1 is repeated except that the particulate slurry employed was a 5% aqueous slurry of zinc oxide having a particle size of 200 nm.

EXAMPLE 3

The pigment preparation procedure of Example 1 is repeated except that before recovering the crystals from the aqueous phase of the slurry, 3.75% of Ce(NO$_3$)$_3$ was added and the pH was raised to 10 with aqueous sodium hydroxide.

EXAMPLE 4

The procedure of Example 2 is repeated except that before recovering the crystals from the aqueous phase of the slurry, 3.75% of Ce(NO$_3$)$_3$ was added and the pH was raised to 10 with aqueous sodium hydroxide.

EXAMPLE 5

The procedure of Example 2 is repeated except that before recovering the crystals from the aqueous phase of the slurry, 3.75% of aluminum nitrate is added and the pH is raised to 7 with aqueous sodium hydroxide.

EXAMPLE 6

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

The hydrolysis reaction under these conditions generally takes about 80 minutes for the BiOCl formation to be complete. After about 72 minutes had elapsed, 360 ml of an aqueous slurry containing 5% of microfine titanium dioxide was introduced into the aqueous bismuth oxychloride crystal slurry and then the hydrolysis reaction was allowed to continue to completion. This took about an additional 8 minutes. After being maintained at that pH for about 15 minutes, the resulting pigment was recovered and dried at 120 degrees C. The dried pigment can be formulated into a powder eye shadow as follows:

| Ingredients | wt parts |
| --- | --- |
| Mearltalc TCA ® (Talc) | 18 |
| Mearlmica ® SVA (Mica) | 20 |
| Magnesium Myristate | 5 |
| Silica | 2 |
| Cloisonné ® Red 424C (red TiO$_2$-coated mica) | 20 |
| Cloisonné ® Violet 525C (violet TiO$_2$-coated mica) | 13 |
| Cloisonné ® Nu-Antique Blue 626CB (TiO$_2$-coated mica/iron oxide-coated mica) | 2 |
| Cloisonné ® Cerise Flambé 550Z (iron oxide-coated mica) | 2 |
| Preservatives & Antioxidant | q.s. |

Then 7 parts of octyl palmitate and 1 part of isostearyl neopentanoate are heated and mixed until uniform, at which time the resulting mixture is sprayed into the dispersion and the blending continued. The blended material is pulverized and then 5 parts of Cloisonne Red 424C and 5 parts of the coated BiOCl added and mixed until a uniform powder eye shadow is obtained.

EXAMPLE 7

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

The hydrolysis reaction under these conditions generally takes about 80 minutes for the BiOCl formation to be complete. After about 72 minutes had elapsed, 360 ml of an aqueous slurry containing 5% of microfine titanium dioxide was introduced into the aqueous bismuth oxychloride crystal slurry and then the hydrolysis reaction was allowed to continue to completion. This took about an additional 8 minutes. After being maintained at that pH for about 15 minutes, the resulting pigment was recovered and dried at 120 degrees C. The dried pigment can be formulated into a lipstick as follows.

The following amounts of the listed ingredients are placed into a heated vessel and the temperature raised to 85±3° C.

| | wt parts |
|---|---|
| Candelilla Wax | 2.75 |
| Carnauba Wax | 1.25 |
| Beeswax | 1.00 |
| Ceresine Wax | 5.90 |
| Ozokerite Wax | 6.75 |
| Microcrystalline Wax | 1.40 |
| Oleyl Alcohol | 3.00 |
| Isostearyl Palmitate | 7.50 |
| Isostearyl Isostearate | 5.00 |
| Caprylic/Capric Triglyceride | 5.00 |
| Bis-Diglycerylpolyalcohol Adipate | 2.00 |
| Acetylated Lanolin Alcohol | 2.50 |
| Sorbitan Tristearate | 2.00 |
| Aloe Vera | 1.00 |
| Castor Oil | 37.50 |
| Red 6 Lake | 0.25 |
| Tocopheryl Acetate | 0.20 |
| Phenoxyethanol, Isopropylparaben, and butylparaben | 1.00 |
| Antioxidant | q.s. |

A mixture of 13 parts of the coated BiOCl and 1 part of kaolin are added and mixed until all of the BiOCl is well dispersed. Fragrance is added as desired and mixed with stirring. The resulting mixture is poured into molds at 75±5° C., allowed to cool and flamed into lipsticks.

EXAMPLE 8

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

The hydrolysis reaction under these conditions generally takes about 80 minutes for the BiOCl formation to be complete. After about 72 minutes had elapsed, 360 ml of an aqueous slurry containing 5% of microfine zinc oxide was introduced into the aqueous bismuth oxychloride crystal slurry and then the hydrolysis reaction was allowed to continue to completion. This took about an additional 8 minutes. After being maintained at that pH for about 15 minutes, the resulting pigment was recovered and dried at 120 degrees C. The dried pigment can be formulated into a powder eye shadow as follows:

The following materials are thoroughly blended and dispersed:

| Ingredients | wt parts |
|---|---|
| Mearltalc TCA ® (Talc) | 18 |
| Mearlmica ® SVA (Mica) | 20 |
| Magnesium Myristate | 5 |
| Silica | 2 |
| Cloisonné ® Red 424C (red TiO$_2$-coated mica) | 20 |
| Cloisonné ® Violet 525C (violet TiO$_2$-coated mica) | 13 |
| Cloisonné ® Nu-Antique Blue 626CB (TiO$_2$-coated mica/iron oxide-coated mica) | 2 |

-continued

| Ingredients | wt parts |
|---|---|
| Cloisonné ® Cerise Flambé 550Z (iron oxide-coated mica) | 2 |
| Preservatives & Antioxidant | q.s. |

Then 7 parts of octyl palmitate and 1 part of isostearyl neopentanoate are heated and mixed until uniform, at which time the resulting mixture is sprayed into the dispersion and the blending continued. The blended material is pulverized and then 5 parts of Cloisonne Red 424C and 5 parts of the coated BiOCl added and mixed until a uniform powder eye shadow is obtained.

EXAMPLE 9

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

The hydrolysis reaction under these conditions generally takes about 80 minutes for the BiOCl formation to be complete. After about 72 minutes had elapsed, 360 ml of an aqueous slurry containing 5% of microfine zinc oxide was introduced into the aqueous bismuth oxychloride crystal slurry and then the hydrolysis reaction was allowed to continue to completion. This took about an additional 8 minutes. After being maintained at that pH for about 15 minutes, the resulting pigment was recovered and dried at 120 degrees C. The dried pigment can be formulated into a lipstick as follows.

The following amounts of the listed ingredients are placed into a heated vessel and the temperature raised to 85±3° C.

| | wt parts |
|---|---|
| Candelilla Wax | 2.75 |
| Carnauba Wax | 1.25 |
| Beeswax | 1.00 |
| Ceresine Wax | 5.90 |
| Ozokerite Wax | 6.75 |
| Microcrystalline Wax | 1.40 |
| Oleyl Alcohol | 3.00 |
| Isostearyl Palmitate | 7.50 |
| Isostearyl Isostearate | 5.00 |
| Caprylic/Capric Triglyceride | 5.00 |
| Bis-Diglycerylpolyalcohol Adipate | 2.00 |
| Acetylated Lanolin Alcohol | 2.50 |
| Sorbitan Tristearate | 2.00 |
| Aloe Vera | 1.00 |
| Castor Oil | 37.50 |
| Red 6 Lake | 0.25 |
| Tocopheryl Acetate | 0.20 |
| Phenoxyethanol, Isopropylparaben, and butylparaben | 1.00 |
| Antioxidant | q.s. |

A mixture of 13 parts of the coated BiOCl and 1 part of kaolin are added and mixed until all of t he BiOCl is well dispersed. Fragrance is added as desired and mixed with stirring. The resulting mixture is poured into molds at 75±5° C., allowed to cool and flamed into lipsticks.

Various changes and modifications can be made in the process and products of this invention without departing from the spirit and scope thereof. The various embodiments which were disclosed herein were for the purpose of further illustrating the invention but were not intended to limit it.

What is claimed is:

1. An effect pigment which comprises bismuth oxychloride crystals having a particulate embedded at about the surface thereof, wherein the particulate is microfine zinc oxide or titanium dioxide.

2. The effect pigment of claim 1 in which the particulate is about 1 to 20 weight percent of the total weight of the pigment.

3. The effect pigment of claim 2 in which the particulate is about 5 to 15 weight percent of the total weight of the pigment.

4. The effect pigment of claim 1 in which the particulate is zinc oxide.

5. The effect pigment of claim 4 in which the particulate is about 1 to 20 weight percent of the total weight of the pigment.

6. The effect pigment of claim 5 in which the particulate is about 5 to 15 weight percent of the total weight of the pigment.

7. The effect pigment of claim 1 in which the particulate is titanium dioxide.

8. The effect pigment of claim 7 in which the particulate is about 1 to 20 weight percent of the total weight of the pigment.

9. The effect pigment of claim 8 in which the particulate is about 5 to 15 weight percent of the total weight of the pigment.

10. In a coating composition including a pigment, the improvement which comprises said pigment being an effect pigment of claim 1.

11. In a plastic composition including a pigment, the improvement which comprises said pigment being an effect pigment of claim 1.

12. In a cosmetic composition including a pigment, the improvement which comprises said pigment being an effect pigment of claim 1.

13. A method of producing a bismuth oxychloride pigment which comprises combining a soluble bismuth salt and chloride ions in an aqueous medium under hydrolyzing conditions to form an aqueous dispersion of bismuth oxychloride crystals, and when about 80 to 95% of crystals formation is complete, adding a particulate to the aqueous medium, wherein the particulate is microfine zinc oxide or titanium dioxide.

14. The process of claim 13 in which the amount of particulate is about 1 to 20 weight percent based on the weight of the bismuth salt.

15. The process of claim 14 in which the amount of particulate is about 5 to 15 weight percent based on the weight of the bismuth salt.

16. The process of claim 13 in which the particulate is zinc oxide.

17. The process of claim 16 in which the amount of particulate is about 1 to 20 weight percent based on the weight of the bismuth salt.

18. The process of claim 16 in which the amount of particulate is about 5 to 15 weight percent based on the weight of the bismuth salt.

19. The process of claim 13 in which the particulate is titanium dioxide.

20. The process of claim 19 in which the amount of particulate is about 1 to 20 weight percent based on the weight of the bismuth salt.

21. The process of claim 20 in which the amount of particulate is about 5 to 15 weight percent based on the weight of the bismuth salt.

22. A method of producing a bismuth oxychloride pigment which comprises combining a soluble bismuth salt and chloride ions in an aqueous medium under hydrolyzing conditions to form an aqueous dispersion of bismuth oxychloride crystals, adding a microfine zinc oxide or titanium dioxide particulate to the aqueous dispersion, combining a salt of aluminum or a rare earth metal with the particulate-containing dispersion, and raising the pH.

23. The process of claim 22 in which the salt combined with the particulate-containing dispersion is a nitrate.

24. The process of claim 23 in which the rare earth metal is cerium and the pH is raised to at least about 10.

25. The process of claim 23 in which the salt combined with the particulate-containing dispersion is aluminum nitrate and the pH is raised to at least about 7.

* * * * *